US00PP18754P3

(12) United States Plant Patent
Houbraken

(10) Patent No.: US PP18,754 P3
(45) Date of Patent: Apr. 22, 2008

(54) ***ASTERISCUS MARITIMUS* PLANT NAMED 'ASMAGO'**

(50) Latin Name: *Asteriscus maritimus*
Varietal Denomination: Asmago

(75) Inventor: Anna M. W. P. Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 2 days.

(21) Appl. No.: 11/474,688

(22) Filed: Jun. 26, 2006

(65) Prior Publication Data

US 2007/0300346 P1 Dec. 27, 2007

(51) Int. Cl.
*A01H 5/00* (2006.01)

(52) U.S. Cl. ..... Plt./263

(58) Field of Classification Search ..... Plt./263, Plt./355
See application file for complete search history.

*Primary Examiner*—Kent Bell
*Assistant Examiner*—June Hwu
(74) *Attorney, Agent, or Firm*—Bruce Vrana

(57) ABSTRACT

A new and distinct cultivar of *Asteriscus maritimus* plant named 'Asmago' characterized by its earliness, flat mounding growth habit, large golden yellow flowers, silvery colored leaves and good branching.

1 Drawing Sheet

Latin name of the genus and species of the plant claimed: *Asteriscus maritimus.*
Varietal denomination: 'Asmago'.

BACKGROUND OF THE NEW PLANT

The present invention relates to a new and distinct cultivar of *Asteriscus* plant botanically known as *Asteriscus maritimus* and referred to by the cultivar name 'Asmago'.

The new cultivar is a product of a planned breeding program conducted by the inventor in Enkhuizen, Netherlands. The new cultivar is an early flowering plant with a flat growth habit, good branching, large flowers, and silvery foliage with flowers all summer.

The new *Asteriscus* originated from a cross-pollination made by the inventor in September 2000 of a proprietary selection of *Asteriscus maritimus* identified as code number 'A231-1' not patented, as the female, or seed parent, with a proprietary selection of *Asteriscus maritimus* identified as code number 'A323-1,' not patented, as the male, or pollen parent. 'A231-1' is later flowering, has a more upright plant habit, and is not branching when compared to the new *Asteriscus*. 'A323-1' is not floriferous and has smaller flowers with shorter petals when compared to the new *Asteriscus*. The new *Asteriscus* was selected as a single plant from the resulting progeny of the cross-pollination in a controlled environment in Enkhuizen, Netherlands in August 2001.

Asexual reproduction of the new cultivar by terminal vegetative cuttings since August 2001, in Enkhuizen, Netherlands has shown that the unique features of this new *Asteriscus* are stable and reproduced true to type in successive generations.

DESCRIPTION OF THE DRAWING

This new *Asteriscus* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Asteriscus* plant. The data which defines these characteristics were collected from asexual reproductions carried out in Enkhuizen, The Netherlands. The plant history was taken on 20 weeks old plants, grown in the field in Enkhuizen, The Netherlands with day temperatures ranging from 16 to 30 degree C., and night temperatures ranging from 10 to 16 degrees Celsius.

Color references are primarily to The R.H.S. Colour Chart of The Royal Horticultural Society of London where general terms of ordinary dictionary significance are used.

TABLE 1

DIFFERENCES BETWEEN THE NEW CULTIVAR 'ASMAGO' AND TWO SIMILAR CULTIVARS

| | 'Asmago' | 'Compact' Open propagated variety (Not patented) | 'Golden Dollar' (Not patented) |
|---|---|---|---|
| Earliness of flowering | 2 weeks earlier | Later | Later |
| Foliage color | Silver 137B Pubescent | Dark green 147A | Dark green 147A |
| Flower color | Bright yellow 9A | Golden yellow 14A | Golden 14A |
| Plant habit | Spreading | Compact | Compact |

The plant:

*Classification.*—Botanical: *Asteriscus maritimus* 'Asmago'.

*Parentage.*—Female parent: Proprietary selection of *Asteriscus maritimus* identified as code number 'A231-1,' not patented. Male parent: Proprietary selection of *Asteriscus maritimus* identified as code number 'A323-1,' not patented.

Propagation:
*Type cuttings.*—Terminal vegetative cuttings.
*Time to initiated roots.*—7 days at air temperature of 21 degrees C.
*Time to develop roots.*—7 days at air temperature of 18 degrees C.
*Root description.*—Fine, fibrous.
*Rooting habit.*—Freely branching.

Plant description:
*Growth habit.*—Start; low and compact, later spreading.
*Plant height.*—16–18 cm.
*Plant diameter* (*area of spread*).—60 cm.
*Vigor.*—Spreading, moderate growing.
*Strength.*—Very good.
*Branching character.*—Freely branching with lateral branches potentially developing at every node, plant do not require pinching.
*Crop time.*—About 10 weeks are required to produce a finished flowering plant in a 10.5 cm container from a good developed cutting.

Lateral branch/stem:
*Diameter.*—4 mm.
*Length.*—25 cm.
*Shape.*—Round.
*Anthocyanin pigmentation.*—Absent.
*Texture.*—Glabrous, soft hairs.
*Length of internode.*—2 cm.
*Pubescence.*—Soft hairs.
*Color.*—144C.

The foliage:
*Arrangement.*—Alternate, single.
*Quantity* (*#leaves/branch*).—20–30.
*Shape of leaf.*—Oblanceolate.
*Leaf apex.*—Obtuse.
*Leaf base.*—Attenuate.
*Leaf margin.*—Entire.
*Texture.*—Coarse, granular.
*Pubescence.*—Present upper and lower side.
*Length.*—2–4 cm.
*Width.*—5–7 mm.
*Depth of incision.*—No incision.
*Color young foliage.*—Upper side: 137A. Lower side: 137B. Color fully expanded foliage Upper side: 137B. Lower side: 137C.
*Petiole.*—Absent.
*Venation.*—Shape: Absent.
*Leaf.*—Lower surface: Densely pubescent. Hair length on lower surface: 1.5 mm. Hair length on edge of leaf (margin) and on veins of lower surface: Varies from 1.5–5 mm. Upper surface: Little pubescent. Hair length on upper surface: 0.5 mm.
*Hair color.*—N155A.

Flower bud:
*Peduncle.*—Length: 0.5–2.0 cm. Strength: Strong. Diameter: 2 mm. Texture: Coarse, granular, pubescent. Color: 144C.
*Size of the bud.*—Length: 10 mm. Diameter: 8–10 mm.
*Shape.*—Ovoid.
*Color.*—12B.

Inflorescence:
*Appearance.*—Daisy-like composite inflorescence form; actinomorphic.
*Lastingness.*—About 2 weeks per inflorescence.
*Diameter inflorescence.*—3.5–4 cm.
*Diameter disc.*—1.3 cm.
*Receptacle height.*—5 mm.
*Involucre/phyllaries.*—Shape: Ligulate. Apex: Rounded. Margin: Entire.
*Length.*—Outer whorl: 12–16 mm. Inner whorl: 9–10 mm.
*Width.*—Outer whorl: 4–5 mm. Inner whorl: 3 mm.
*Color.*—Upper: 137A. Lower: 137A.
*Number per infl.*—16 in two whorls.
*Texture.*—Pubescent.
*Fragrance.*—Not detected.
*Quantity of inflorescences/branch.*—15.
*Flowering period.*—April until October in Northern Hemisphere, plants flower continuously.

Ray florets:
*Shape of ray florets.*—Ligulate.
*Apex.*—Tri-dentate.
*Base.*—Attenuate.
*Margin.*—Entire.
*Color.*—Young flower: 9A. Fully open flower: 9A.
*No. of ray florets per inflorescence.*—21 in a single whorl.
*Size.*—Length: 14–17 mm. Width: 4 mm.
*Texture.*—Smooth, velvety.

Disc florets:
*Shape of disc florets.*—Tubular.
*Color.*—14A.
*Length of disc floret.*—5 mm.
*Width of disc floret.*—1 mm.
*Number of disc florets/flower.*—140–160.

Androecium: Present on disc florets only.
*Anther color.*—14A.
*Pollen color.*—14A.
*Amount of pollen.*—Low.
*Number of stamen.*—5.
*Stamen shape.*—Oblong.
*Anther size.*—2 mm.

Gynoecium: Present on ray and disc florets.
*Pistil number/floret.*—1.
*Pistil length.*—2 mm.
*Style color.*—13A.
*Style length.*—0.5 mm.
*Stigma color.*—14A.
*Stigma shape.*—Bipartite.
*Ovary color.*—1D.

Seed: Seed production is not observed.

Disease resistance: No susceptibility nor resistance to fungal, bacterial or viral pathogens has been noted. Material is free of virus.

Heat/cold tolerance: Plants of the new *Asteriscus* have demonstrated good tolerance to high and low temperatures.

What is claimed is:

1. A new and distinct variety of *Asteriscus maritimus* plant, substantially as herein illustrated and described.

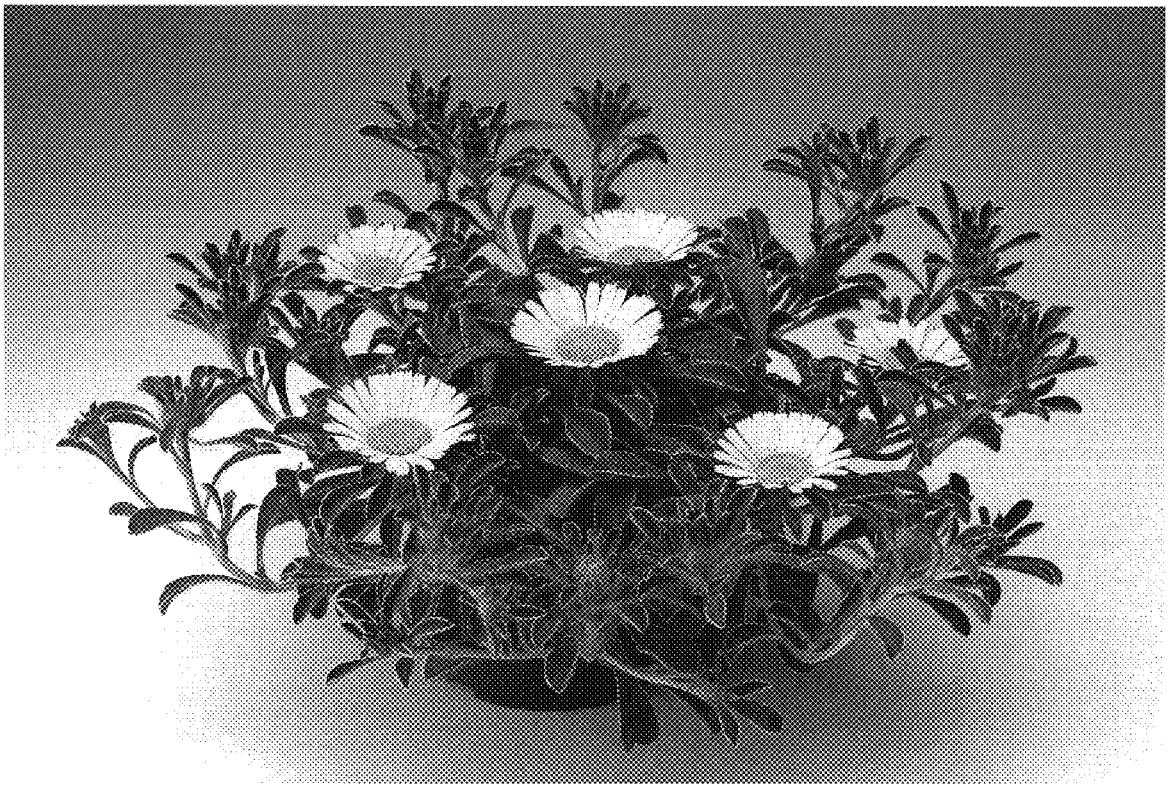

* * * * *